US00PP19741P2

(12) United States Plant Patent
Heinrich

(10) Patent No.: US PP19,741 P2
(45) Date of Patent: Feb. 17, 2009

(54) ***PHLOX* PLANT NAMED 'WESPOFU'**

(50) Latin Name: *Phlox hybrida*
Varietal Denomination: Wespofu

(75) Inventor: Westhoff Heinrich, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 11/983,745

(22) Filed: Nov. 12, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Phlox* plant named 'Wespofu', characterized by its compact, upright and mounding plant habit; freely branching growth habit; freely and continuous flowering habit; long flowering period; red purple and white bi-colored fringed flowers; and good garden performance.

1 Drawing Sheet

Botanical designation: *Pholox hybrida.*

Cultivar denomination: 'Wespofu'.

BACKGROUND OF THE INVENTION

The present invention relates to a new and distinct cultivar of *Phlox* botanically known as *Phlox hybrida* and hereinafter referred to by the name 'Wespofu'.

The new *Phlox* is a product of a planned breeding program conducted by the Inventor in Südlohn, Germany. The objective of the breeding program was to create new compact and freely branching *Phlox* cultivars with numerous attractive flowers.

The new *Phlox* originated from a cross-pollination made by the Inventor in 2004, in Südlohn, Germany, of a proprietary selection of *Phlox hybrida* identified as code number 04P002, not patented, as the female, or seed, parent with a proprietary selection of *Phlox hybrida* identified as code number 04P022, not patented, as the male, or pollen, parent. The new *Phlox* was discovered and selected by the Inventor as a single flowering plant within the progeny of the stated cross-pollination in a controlled environment in Südlohn, Germany in 2005.

Asexual reproduction of the new *Phlox* by vegetative cuttings in a controlled environment in Südlohn, Germany since 2005 has shown that the unique features of this new *Phlox* are stable and reproduced true to type in successive generations.

SUMMARY OF THE INVENTION

The cultivar Wespofu has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wespofu'. These characteristics in combination distinguish 'Wespofu' as a new and distinct cultivar of *Phlox:*

1. Compact, upright and mounding plant habit.
2. Freely branching growth habit.
3. Freely and continuous flowering habit; long flowering period.
4. Red purple and white bi-colored fringed flowers.
5. Good garden performance.

Plants of the new *Phlox* differ from plants of the female parent selection in the following characteristics:

1. Plants of the new *Phlox* are more freely branching than plants of the female parent selection.
2. Plants of the new *Phlox* have lighter green-colored leaves than plants of the female parent selection.
3. Flowers of plants of the new *Phlox* are fringed whereas flowers of plants of the female parent selection are not fringed.
4. Plants of the new *Phlox* and the female parent selection differ in flower color as plants of the female parent selection have lilac pink-colored flowers.

Plants of the new *Phlox* differ from plants of the male parent selection in the following characteristics:

1. Plants of the new *Phlox* are more vigorous than plants of the male parent selection.
2. Plants of the new *Phlox* and the male parent selection differ in flower color as plants of the male parent selection have blue and white bi-colored flowers.

Plants of the new *Phlox* can be compared to plants of the *Phlox* cultivar USPHL304, disclosed in U.S. Plant Pat. No. 17,899. In side-by-side comparisons conducted in Südlohn, Germany, plants of the new *Phlox* differed from plants of the cultivar USPHL304 in the following characteristics:

1. Plants of the new *Phlox* were more compact and more freely branching than plants of the cultivar USPHL304.
2. Plants of the new *Phlox* had stronger lateral branches than plants of the cultivar USPHL304.
3. Flowers of plants of the new *Phlox* were fringed whereas flowers of plants of the cultivar USPHL304 were not fringed.
4. Plants of the new *Phlox* and the cultivar USPHL304 differed in flower color as plants of the USPHL304 had lavender-colored flowers with a white and purple-colored star pattern at the center.

Plants of the new *Phlox* can also be compared to plants of the *Phlox* cultivar USPHL03, disclosed in U.S. Plant Pat. No. 15,846. In side-by-side comparisons conducted in Südlohn, Germany, plants of the new *Phlox* differed from plants of the cultivar USPHL03 in the following characteristics:

1. Plants of the new *Phlox* were more compact and had shorter internodes than plants of the cultivar USPHL03.
2. Plants of the new *Phlox* had stronger lateral branches than plants of the cultivar USPHL03.
3. Flowers of plants of the new *Phlox* were fringed whereas flowers of plants of the cultivar USPHL03 were not fringed.
4. Plants of the new *Phlox* and the cultivar USPHL03 differed in flower color as plants of the USPHL03 had dark purple-colored flowers with a red-colored star pattern at the center.

BRIEF DESCRIPTION OF THE PHOTOGRAPH

The accompanying colored photograph illustrates the overall appearance of the new *Phlox,* showing the colors as true as it is reasonably possible to obtain in colored reproductions of this type. Colors in the photograph may differ slightly from the color values cited in the detailed botanical description which accurately describe the colors of the new *Phlox.* The photograph comprises a side perspective view of a typical flowering plant of 'Wespofu' grown in a container.

DETAILED BOTANICAL DESCRIPTION

The aforementioned photograph and following observations, measurements and values describe plants grown in Südlohn, Germany, under commercial practice during the summer in a glass-covered greenhouse with day temperatures ranging from 20° C. to 25° C., night temperatures ranging from 16° C. to 18° C. and light levels ranging from 3,000 lux to 50,000 lux. Rooted young plants were grown for about 20 weeks when the photograph and description were taken. In the following description, color references are made to The Royal Horticultural Society Colour Chart, 2001 Edition, except where general terms of ordinary dictionary significance are used.

Botanical classification: *Phlox hybrida* cultivar Wespofu.

Parentage:

*Female, or seed, parent.*—Proprietary selection of *Phlox hybrida* identified as code number 04P002, not patented.

*Male, or pollen, parent.*—Proprietary selection of *Phlox hybrida* identified as code number 04P022, not patented.

Propagation:

*Type.*—By vegetative cuttings.

*Time to initiate roots, summer.*—About 10 to 14 days at temperatures of 20° C.

*Time to initiate roots, winter.*—About 16 to 18 days at temperatures of 20° C.

*Time to produce a rooted young plant, summer.*—About 21 to 24 days at temperatures of 20° C.

*Time to produce a rooted young plant, winter.*—About 24 to 26 days at temperatures of 20° C.

*Root description.*—Fibrous; color, close to 158A.

*Rooting habit.*—Freely branching; moderately dense to dense.

Plant description:

*Plant form/habit.*—Compact, upright and mounded plant habit; outwardly spreading; vigorous growth habit. Freely branching habit with lateral branches developing at every node; pinching enhances branching potential.

*Plant height.*—About 20 cm to 22 cm.

*Plant width* (*spread*).—About 33 cm.

*Lateral branches.*—Length: About 12.7 cm. Diameter: About 2.8 mm. Internode length: About 1.65 cm. Strength: Strong. Texture: Pubescent; viscid. Color: 144A.

Foliage description:

*Arrangement.*—Alternate, simple; sessile.

*Length.*—About 2.8 cm.

*Width.*—About 8 mm.

*Shape.*—Lanceolate.

*Apex.*—Acute.

*Base.*—Obtuse.

*Margin.*—Entire.

*Texture, upper and lower surfaces.*—Pubescent.

*Venation pattern.*—Pinnate.

*Color.*—Developing leaves, upper surface: 146A. Developing leaves, lower surface: 146B. Fully expanded leaves, upper surface: 146A to 146B; venation, 146A to 146B. Fully expanded leaves, lower surface: 137C; venation, 137C.

Flower description:

*Flower type/habit.*—Single fringed salverform flowers arranged in terminal cymes; flowers face upward to outward. Freely flowering habit with about six flowers per cyme.

*Fragrance.*—None detected.

*Natural flowering season.*—Long flowering period; continuously flowering from April to autumn in Germany. Flowers not persistent.

*Postproduction longevity.*—Flowers last about five days on the plant.

*Flower buds.*—Height: About 1.5 cm. Diameter: About 2.7 mm. Shape: Oblong Color: 196D; towards apex, N81A.

*Inflorescence height.*—About 11.2 cm.

*Inflorescence diameter.*—About 12.7 cm.

*Flower diameter.*—About 2.7 cm.

*Flower depth.*—About 1.7 cm.

*Petals.*—Quantity per flower: Typically five in a single whorl; petals fused at the base into a narrow tube. Lobe length: About 1.5 cm. Lobe width: About 1.1 cm. Shape: Obovate. Apex: Cuspidate. Margin: Irregularly fringed. Texture, upper and lower surfaces: Smooth, glabrous. Color: Developing and fully expanded petal lobes, upper surface: Mixture of 71A and N74A; towards the margin, close to 155D. Developing and fully expanded petal lobes, lower surface: 76D; color becoming closer to 85D with development. Eye: N88B; spots, 79A. Throat: 149D; fine lines, 71A. Tube: 1D.

*Sepals.*—Quantity per flower: Typically five in a single whorl, fused at base; tubular in shape. Length: About 1.1 cm. Width: About 1.1 mm. Shape: Acicular. Apex: Acute. Margin: Entire. Texture, upper and lower surfaces: Densely pubescent. Color, upper and lower surfaces: 138A.

*Peduncles.*—Length: About 9 mm to 17 mm. Diameter: About 2.5 mm. Strength: Strong, flexible. Texture: Pubescent. Color: 144A.

*Pedicels.*—Length: About 3 mm to 5 mm. Diameter: About 1 mm. Strength: Strong, flexible. Texture: Pubescent. Color: 144B.

*Reproductive organs.*—Stamens: Quantity per flower: Typically five. Filament length: Less than 1 mm. Anther shape: Lanceolate. Anther length: About 1.5 mm. Anther width: About 0.7 mm. Anther color: 13A. Pollen amount: Moderate. Pollen color: 17A. Pistils: Quantity per flower: One. Pistil length: About 4.3 mm. Stigma shape: Three-parted. Stigma color: N144A to N144B. Style length: Less than 1 mm. Style color: 144B. Ovary color: 144B.

*Seeds.*—Quantity per flower: Typically three. Length: About 2.5 mm. Diameter: About 2 mm. Color: N200A to N200B.

Disease/pest resistance: Plants of the new *Phlox* have not been noted to be resistant to pathogens and pests common to *Phlox*.

Garden performance: Plants of the new *Phlox* have been observed to have good garden performance and tolerate rain, wind and temperatures from about 5° C. to about 30° C.

It is claimed:

1. A new and distinct *Phlox* plant named 'Wespofu' as illustrated and described.

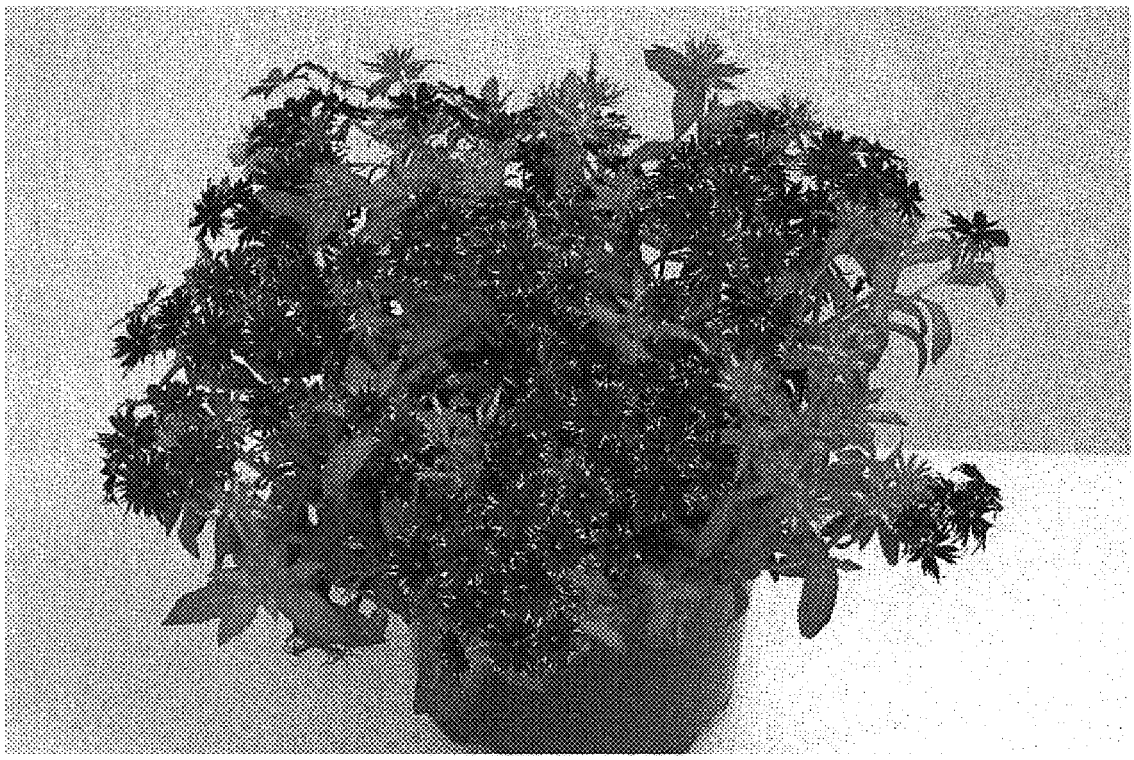

* * * * *